United States Patent [19]

Esrock

[11] Patent Number: 5,242,300
[45] Date of Patent: Sep. 7, 1993

[54] NOZZLE FOR DENTAL TOOL

[76] Inventor: Bernard S. Esrock, 320 Dungate Dr., Chesterfield, Mo. 63017

[21] Appl. No.: 995,894

[22] Filed: Dec. 23, 1992

[51] Int. Cl.⁵ .................................. A61G 17/02
[52] U.S. Cl. ............................ 433/80; 433/126
[58] Field of Search ................ 433/80, 82, 84, 85, 433/126, 127; 604/257, 258, 261, 140

[56] References Cited

U.S. PATENT DOCUMENTS

| | | | |
|---|---|---|---|
| 3,254,646 | 6/1966 | Staunt et al. | 128/224 |
| 3,698,088 | 10/1972 | Austin, Jr. | 433/80 |
| 3,874,083 | 4/1975 | Buckley | 32/22 |
| 4,026,025 | 5/1977 | Hunt | 32/22 |
| 4,068,664 | 1/1978 | Sharp et al. | 128/276 |
| 4,108,178 | 8/1978 | Betush | 128/224 |
| 4,149,315 | 4/1979 | Page, Jr. et al. | 32/22 |
| 4,214,871 | 7/1980 | Arnold | 433/216 |
| 4,248,589 | 2/1981 | Lewis | 433/80 |
| 4,412,402 | 11/1983 | Gallant | 51/439 |
| 4,462,803 | 7/1984 | Landgraf et al. | 433/88 |
| 4,492,575 | 1/1985 | Mabille | 51/439 |
| 4,522,597 | 6/1985 | Gallant | 433/216 |
| 4,595,365 | 6/1986 | Edel et al. | 433/216 |
| 4,675,004 | 6/1987 | Hadford et al. | 604/44 |
| 4,676,749 | 6/1987 | Mabille | 433/88 |
| 4,696,645 | 9/1987 | Saupe et al. | 433/125 |
| 4,975,054 | 12/1990 | Esrock | 433/80 |
| 4,984,984 | 1/1991 | Esrock | 433/88 |
| 5,049,071 | 9/1991 | Davis et al. | 433/80 |

FOREIGN PATENT DOCUMENTS 2213732 11/1991 United Kingdom .

OTHER PUBLICATIONS

Representative drawing of prior art syringe tip manufactured and sold by applicant prior to Dec. 23, 1991.

Primary Examiner—Gene Mancene
Assistant Examiner—Thomas Price
Attorney, Agent, or Firm—Senniger, Powers Leavitt & Roedel

[57] ABSTRACT

A nozzle for use with a dental tool having a hand-piece comprising first and second fluid conduits for delivering first and second fluids to a discharge end of the hand-piece. The nozzle is releasably engageable with the discharge end of the hand-piece and comprises an inner tube and an outer tube each having an intake end and a discharge end. The tubes define first and second fluid passages having coaxial intake ports for fluid communication with the first and second fluid conduits and coaxial discharge ports for pressurized delivery of the first and second fluids to the teeth of the patient. The intake end of the inner tube extends axially from the intake end of the outer tube and is connected to the first conduit when the nozzle is engaged with the hand-piece so that fluid discharged from the first conduit flows through the first passage. The intake end of the outer tube is shaped so that the intake port of the second fluid passage avoids seating against a portion of the hand-piece thereby to maintain a passageway between the intake port of the second fluid passage and the portion of the hand-piece so that fluid flowing through the second conduit flows through the fluid passageway to the second passage.

9 Claims, 1 Drawing Sheet

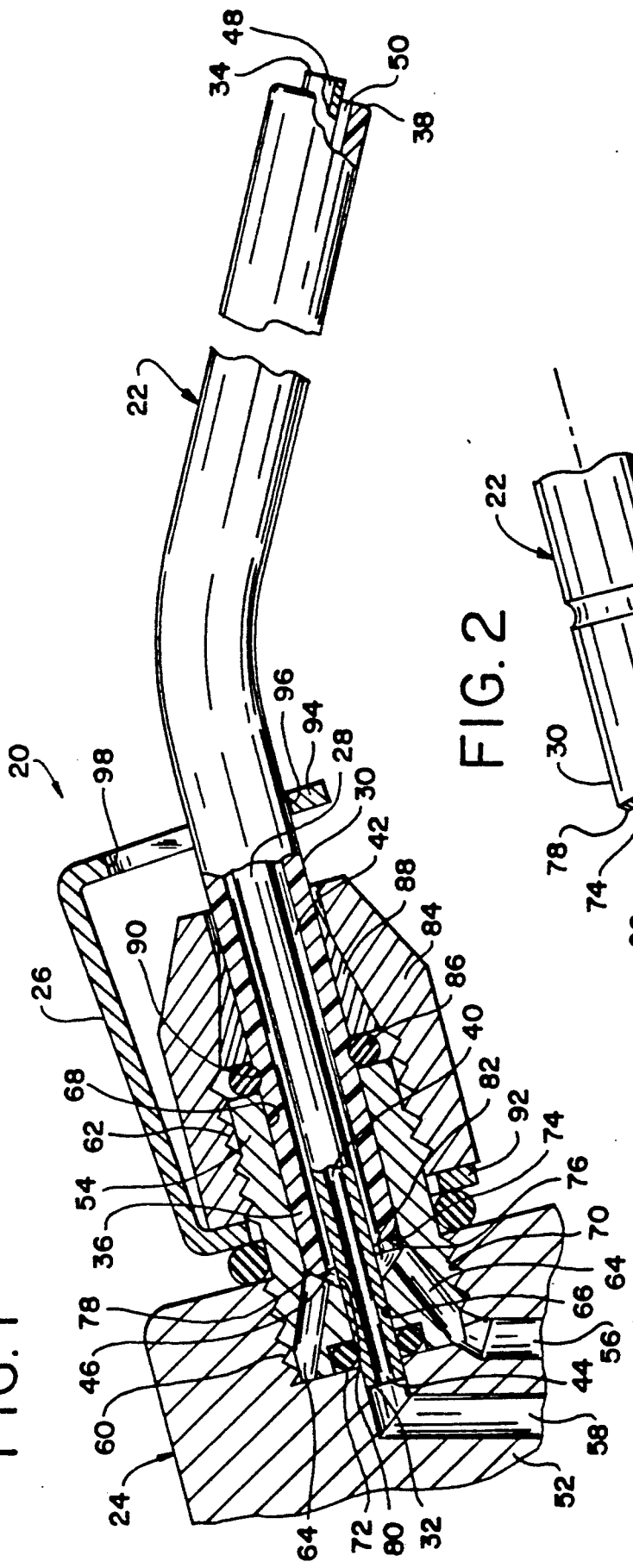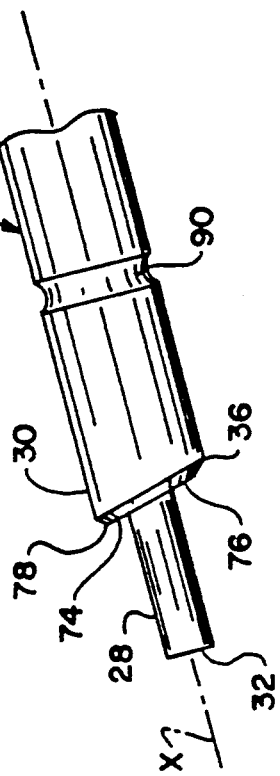

NOZZLE FOR DENTAL TOOL

BACKGROUND OF THE INVENTION

This invention relates to a dental tool, and more particularly to a nozzle for a dental tool for delivering two fluid streams to teeth of a patient.

Air-water syringes are used by dentists and dental technicians for cleaning debris from a patient's teeth and mouth. The teeth and mouth are cleaned by the spraying of a water stream, or an air stream, or a mixed air-water stream from the syringe. A typical air-water syringe has a hand-piece and a nozzle releasably attached to the hand-piece The nozzle has a first passageway through which air away flow and a second passageway through which water away flow. When the nozzle is attached to the hand-piece, the first passageway communicates with an air conduit in the hand-piece and the second passageway communicates with a water conduit. The nozzle is retained in the hand-piece by a retaining collar, attached to a threaded stem in the hand-piece, which compresses an O-ring into a groove on the outer surface of the nozzle to form an interference fit for resisting withdrawal of the nozzle from the hand-piece. Between uses of the syringe, the nozzle must be removed from the hand-piece and sterilized or be replaced with a sterile nozzle.

Disadvantages encountered with such a syringe are the difficulty in readily removing the nozzle from the hand-piece, cleaning the nozzle and sterilizing it. An air-water syringe described in U.S. Pat. No. 4,975,054 (incorporated herein by reference) overcomes these disadvantages by use of a disposable nozzle having first and second fluid passages with coaxial intake ports and coaxial discharge ports. However, when inserted into a hand-piece, the nozzle may seat against a wall of the hand-piece, thereby blocking flow through one of the intake ports.

SUMMARY OF THE INVENTION

Among the several objects of this invention may be noted the provision of an improved nozzle for a dental tool; the provision of such a nozzle which is configured to avoid blocking flow through one of the intake ports when connected to the hand-piece; the provision of such a nozzle which is of relatively simple and inexpensive construction; and the provision of such a nozzle which is disposable.

Generally, the nozzle of this invention is for use with a dental tool having a hand-piece comprising first and second fluid conduits for delivering first and second fluids to a discharge end of the hand-piece. The nozzle is releasably engageable with the discharge end of the hand-piece. It comprises an inner tube and an outer tube each having an intake end and a discharge end. The tubes defining first and second fluid passages having coaxial intake ports for fluid communication with the first and second fluid conduits and coaxial discharge ports for pressurized delivery of the first and second fluids to the teeth of the patient. The intake end of the inner tube extends axially from the intake end of the outer tube and is connected to the first conduit when the nozzle is engaged with the hand-piece so that fluid discharged from the first conduit flows through the first passage. The intake end of the outer tube is shaped so that the intake port of the second fluid passage avoids seating against a portion of the hand-piece thereby to maintain a passageway between the intake port of the second fluid passage and the portion of the hand-piece so that fluid flowing through the second conduit flows through the fluid passageway to the second passage.

Other objects and features will be in part apparent and in part pointed out hereinafter.

BRIEF DESCRIPTION OF THE DRAWINGS

FIG. 1 is a side elevation view of a nozzle of the present invention inserted into a hand-piece of a dental syringe with portions broken away to show detail; and FIG. 2 is an elevation view showing the intake end of the nozzle.

Corresponding reference numerals indicate corresponding parts throughout the several views of the drawings.

DETAILED DESCRIPTION OF THE PREFERRED EMBODIMENT

A dental tool for delivering a mixed stream of two fluids to teeth of a patient constructed according to the principles of this invention is indicated generally at 20 in FIG. 1. The dental tool 20 comprises a nozzle 22, a hand-piece 24, and a resiliently flexible clip 26 adapted for releasably retaining the nozzle 22 in the hand-piece 24.

The nozzle 22 has an inner tube 28 and an outer tube 30. The inner tube 28 has an intake end 32 and a discharge end 34 and the outer tube 30 has an intake end 36 and a discharge end 38. The tubes define first and second fluid passages, constituting inner and outer fluid passages 40 and 42, having coaxial intake ports 44 and 46, respectively, and coaxial discharge ports 48 and 50, respectively. The intake end 32 of the inner tube 28 extends axially from the intake end 36 of the outer tube 30. Preferably, the inner tube 28 is made of stainless steel and the outer tube is made of polyvinyl chloride. The nozzle 22 is formed by inserting a straight inner tube into a straight outer tube and then bending the two tubes. The bend (curvature) of the nozzle 22 is sufficient to hold the two tubes together without the need for bonding or joining. Thus, the nozzle 22 is simply a tube within a tube which can be constructed easily and inexpensively.

The hand-piece 24 includes a handle portion 52 and a stem 54 extending from a discharge end of the handle portion 52. The handle portion 52 has a first fluid conduit 56 for directing an air stream to the outer fluid passage 42 and a second fluid conduit 58 for directing a liquid stream (e.g., water) to the inner passage 40. The stem 54 has first and second external screw threads 60 and 62, fluid passages 64, a central bore 66 for receiving the intake end 32 of inner tube 28, and a socket 68 for receiving the intake end 36 of the outer tube 30. The first screw thread 60- mates with a threaded bore 70 in the handle portion 52 to secure the stem 54 to the handle portion 52. The fluid passages 64 communicate with the first fluid conduit 56 of handle portion 52 so that the air stream passes therethrough. When the nozzle 22 is inserted into the hand-piece 24, the intake end 32 of inner tube 28 extends through the central bore 66 so that the inner passage 40 communicates with the second fluid conduit 58 of the handle portion 52. With the nozzle 22 so positioned, the intake end 32 of inner tube 28 seats against an O-ring 72 to prevent leakage of water between the handle portion 52 and stem 54.

The intake end 36 of outer tube 30 has an inlet end face 74 which is asymmetrical to the axis X (see FIG. 2)

of the intake ports of the nozzle 22. Preferably, the inlet end face 74 is generally planar and lies in a plane oblique to the axis X. The end face 74 defines a recessed portion 76 of the outer tube 30 and a protruding portion 78 extending axially of the recessed portion 76. When the outer tube 30 is inserted into the socket 68, the protruding portion 78 engages a wall 80 of the socket 68 so that the recessed portion 76 is spaced a distance from the wall 80. The space between the recessed portion 76 and wall 80 defines a passageway 82 connecting the fluid passages 64 of stem 54 to the outer passage 42. Maintaining the space between the recessed portion 76 and wall 80 prevents the intake end 36 of the outer tube 30 from seating (i.e., sealing) against the wall 80 and stopping flow from the fluid passages 64 to the outer passage 42. Although the inlet end face 74 is preferably planar and oblique to the axis X, it is to be understood that the inlet end face 74 may be some other shape which prevents seating against the wall 80. For example, an alternative inlet end face could have one or more notches which prevents at least a portion of it from contacting the wall 80.

The nozzle 22 is releasably secured to the stem 54 by a nut 84 threadable onto the second external threads 62 of stem 54. An O-ring 86 is positioned over the outer conduit 36 and abuts an end of the stem 54 to prevent leakage of the air steam. The nut 84 urges a generally cone-shaped sleeve 88 against the O-ring 86 to hold the O-ring 86 in place The outer tube 30 includes a circumferential groove 90 around its periphery spaced from its intake end 36. The groove 90 is engageable with the O-ring 86 for retaining the nozzle 22 in engagement with the stem 54. Preferably, the nozzle 22 may be inserted into and removed from the stem 54 without loosening the nut 84. Also, the intake end 36 of the outer tube 30 is preferably chamfered or rounded so that as the nozzle 22 is inserted into the stem 54. the chamfered intake end 36 acts as a cam to force the O-ring 86 radially outwardly and the outer tube 30 is pushed through the O-ring 86 until the O-ring 86 aligns with and is seated in the groove 90.

The nozzle 22 may further be retained in the stem 54 by the clip 26. The clip 26 has a base portion 92 secured by the nut 84 to the hand-piece 24 and a contact portion 94 adapted to engage a contact region 96 of the nozzle. The clip 26 acts as a spring to bias the contact portion 94 against the contact region 96 to impart a lateral force to the nozzle 22 to frictionally secure the nozzle 22 to the hand-piece 24. The clip 26 further includes a generally oblong opening 98 through which the nozzle 22 extends. The lower portion of the opening 98 (as viewed in FIG. 1) defines the contact portion 94. Deflecting the clip 26 downwardly with respect to the nozzle 22 disengages the contact portion 94 from the contact region 96 to enable a user to readily remove the nozzle 22 from or insert it into the hand-piece 24.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

I claim:

1. For use with a dental tool having a hand-piece comprising first and second fluid conduits for delivering first and second fluids to a discharge end of the hand-piece, a nozzle releasably engageable with the discharge end of the hand-piece comprising an inner tube and an outer tube each having an intake end and a discharge end, said tubes defining first and second fluid passages having coaxial intake ports for fluid communication with the first and second fluid conduits and coaxial discharge ports for pressurized delivery of the first and second fluids to the teeth of the patient, the intake end of the inner tube extending axially from the intake end of the outer tube and being connected to the first conduit when the nozzle is engaged with the hand-piece so that fluid discharged from the first conduit flows through the first passage, the intake end of the outer tube being chamfered, the intake end of said outer tube also having a generally annular inlet end face having a recessed portion and a protruding portion extending axially from the recessed portion, the protruding portion being engageable with a wall of the hand-piece to maintain the recessed portion spaced from said wall thereby to define a fluid passageway between said recessed portion and said wall so that fluid flowing through the second conduit flows through the fluid passageway to the second passage.

2. A nozzle as set forth in claim 1 wherein the tubes each have an intermediate portion with the intermediate portion of the outer tube surrounding the intermediate portion of the inner tube, said tubes being bent to constrain the first conduit in the second conduit.

3. A nozzle as set forth in claim 1 wherein the outer tube includes a circumferential groove around its periphery and spaced from its intake end, said groove being engageable with an O-ring in the hand-piece for retaining the nozzle in engagement with the hand-piece.

4. A nozzle as set forth in claim 1 wherein the inlet end face of said outer tube is generally planar and lies in a plane oblique to a line coaxial with the intake ports of the first and second fluid passages.

5. For use with a dental tool having a hand-piece comprising first and second fluid conduits for delivering first and second fluids to a discharge end of the hand-piece, a nozzle releasably engageable with the discharge end of the hand-piece comprising an inner tube and an outer tube each having an intake end and a discharge end, said tubes defining first and second fluid passages having coaxial intake ports for fluid communication with the first and second fluid conduits and coaxial discharge ports for pressurized delivery of the first and second fluids to the teeth of the patient, the intake end of the inner tube extending axially from the intake end of the outer tube and being connected to the first conduit when the nozzle is engaged with the hand-piece so that fluid discharged from the first conduit flows through the first passage, the intake end of the outer tube being chamfered and defining a generally annular inlet end face substantially asymmetrical about a line coaxial with the intake ports of the first and second fluid passages for maintaining a space between at least a portion of said inlet end face and a wall of the hand-piece thereby to define a fluid passageway between said portion of said inlet end face and said wall so that fluid flowing through the second conduit flows through the fluid passageway to the second passage.

6. A nozzle as set forth in claim 5 wherein the inlet end face has a recessed portion and a protruding portion extending axially from the recessed portion so that when the nozzle is engaged with the hand-piece the protruding portion is engageable with a wall of the hand-piece to maintain the recessed portion spaced from said wall.

7. A nozzle as set forth in claim 5 wherein the inlet end face of said outer tube is generally planar and lies in a plane oblique to said line.

8. A nozzle as set forth in claim 5 wherein the tubes each have an intermediate portion with the intermediate portion of the outer tube surrounding the intermediate portion of the inner tube, said tubes being bent to constrain the first conduit in the second conduit.

9. A nozzle as set forth in claim 8 wherein the outer tube includes a circumferential groove around its periphery and spaced from its intake end, said groove being engageable with an O-ring in the hand-piece for retaining the nozzle in engagement with the hand-piece.

* * * * *